United States Patent [19]
Schoendorfer et al.

[11] Patent Number: 5,188,588
[45] Date of Patent: Feb. 23, 1993

[54] SINGLE NEEDLE CONTINUOUS HEMAPHERESIS APPARATUS AND METHODS

[75] Inventors: Donald W. Schoendorfer, Santa Ana; Paul R. Prince, Fountain Valley, both of Calif.

[73] Assignee: Baxter Internatonal Inc., Deerfield, Ill.

[21] Appl. No.: 455,794

[22] Filed: Dec. 20, 1989

Related U.S. Application Data

[63] Continuation of Ser. No. 348,166, May 2, 1989, abandoned, which is a continuation of Ser. No. 125,102, Nov. 25, 1987, abandoned.

[51] Int. Cl.$^5$ .............................................. A61M 37/00
[52] U.S. Cl. ........................................... 604/6; 604/4
[58] Field of Search ......................................... 604/4-6, 604/408, 410; 210/927

[56] References Cited

U.S. PATENT DOCUMENTS

| | | |
|---|---|---|
| 3,489,145 | 1/1970 | Judson et al. . |
| 3,655,123 | 4/1972 | Judson et al. . |
| 3,756,234 | 9/1973 | Kopp . |
| 4,061,031 | 12/1977 | Grimsrud .......................... 210/188 |
| 4,187,979 | 2/1980 | Cullis et al. . |
| 4,191,182 | 3/1980 | Popovich et al. . |
| 4,223,672 | 9/1980 | Terman et al. . |
| 4,350,156 | 9/1982 | Malchesky et al. . |
| 4,397,747 | 8/1983 | Ikeda . |
| 4,464,167 | 8/1984 | Schoendorfer et al. . |
| 4,490,134 | 12/1984 | Troutner . |
| 4,514,295 | 4/1985 | Mathieu et al. . |
| 4,596,549 | 6/1986 | Minami . |
| 4,605,503 | 8/1986 | Bilstad et al. . |
| 4,606,826 | 8/1986 | Sano et al. . |
| 4,643,714 | 2/1987 | Brose ..................................... 604/4 |
| 4,648,866 | 3/1987 | Malbrancq et al. ..................... 604/5 |
| 4,680,025 | 7/1987 | Kruger ..................................... 604/6 |
| 4,713,176 | 12/1987 | Schoendorfer ................. 210/782 X |
| 4,747,952 | 5/1988 | Nakano et al. . |
| 4,758,336 | 7/1988 | Bock et al. . |
| 4,770,787 | 9/1988 | Heath et al. . |
| 4,776,837 | 10/1988 | Kopp . |
| 4,776,964 | 10/1988 | Schoendorfer et al. . |
| 4,828,543 | 5/1989 | Weiss et al. . |
| 4,838,865 | 6/1989 | Flank et al. . |

FOREIGN PATENT DOCUMENTS

| | | |
|---|---|---|
| 0156496 | 10/1985 | Japan . |
| 0171749 | 2/1986 | Japan . |
| WO85/04112 | 9/1985 | PCT Int'l Appl. . |
| WO88/05332 | 7/1988 | PCT Int'l Appl. . |

Primary Examiner—Stephen C. Pellegrino
Assistant Examiner—Michael Rafa
Attorney, Agent, or Firm—Paul C. Flattery; Daniel D. Ryan; Bradford R. L. Price

[57] ABSTRACT

Blood separation is accomplished by alternately extracting blood from and reinfusing blood into a donor by way of a single needle while simultaneously and continuously separating the extracted blood into constituents. A harness set applicable to a hemapheresis instrument includes a dual-compartment reservoir. A first compartment stores blood during extraction for supply to the separator during reinfusion. The second compartment stores packed cells during collection for return to the donor during reinfusion. The collection and reinfusion cycles are alternated rapidly to preclude clotting in the un-anticoagulated portion of the harness tubing between the venepuncture needle and the Y-connection with the anticoagulant line.

58 Claims, 5 Drawing Sheets

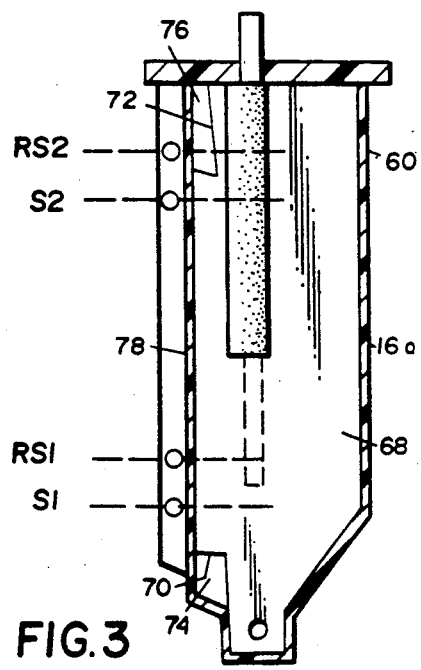
FIG. 3
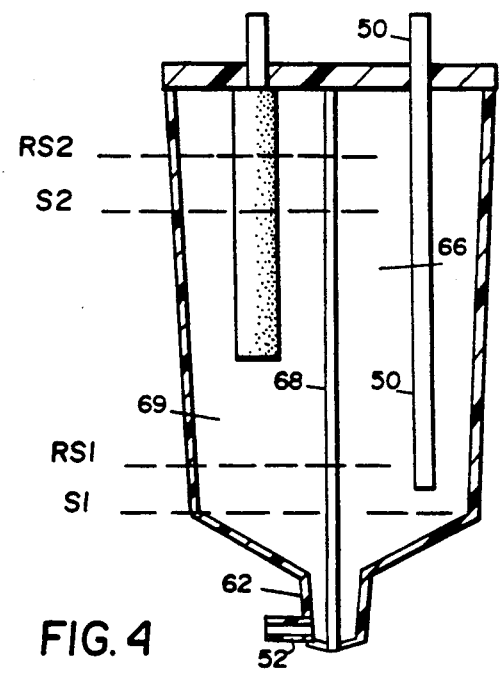
FIG. 4
FIG. 7
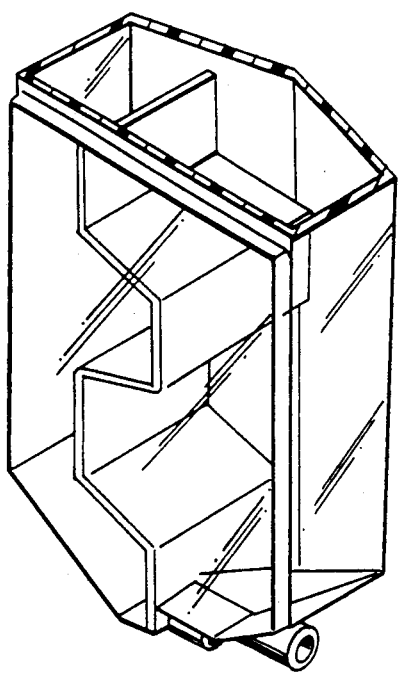
FIG. 8
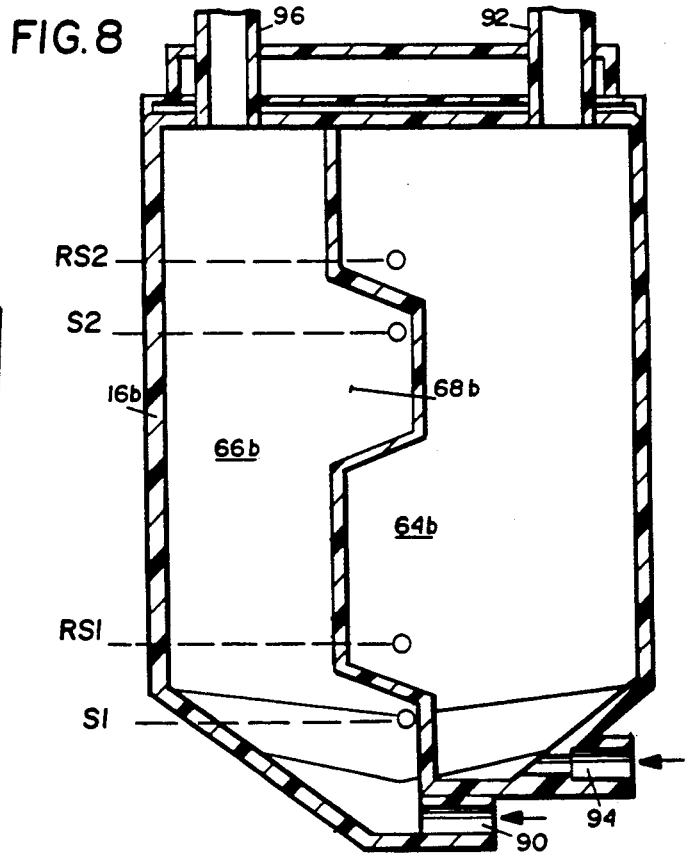

SINGLE NEEDLE CONTINUOUS HEMAPHERESIS APPARATUS AND METHODS

This application is a continuation of application Ser. No. 07/348,166 filed May 2, 1989, abandoned, which is a continuation of application Ser. No. 07/125,102 filed Nov. 25, 1987, abandoned.

The present invention relates to single needle hemapheresis apparatus and methods and particularly relates to apparatus and methods for the continuous separation of blood constituents from whole blood in a single needle hemapheresis system.

There are a number of automated on-line donor hemapheresis systems for separating whole blood into two or more of its constituents including, for example, plasma, blood cell concentrate, and platelet-rich plasma. Such systems are designed to collect a predetermined volume of plasma from a donor using a fully-automated processing program in conjunction with a hemapheresis instrument and a disposable tubing or harness set packaged separately from the instrument. One such system is the AUTOPHERESIS-C Plasmapheresis System manufactured by Baxter Healthcare Corporation, a subsidiary of the assignee of the present invention.

Typically in systems of this general type, the instrument includes a microprocessor for controlling a number of pumps, clamps, detectors, monitoring systems, etc., for automating the collection of whole blood from the donor, separating the blood into plasma and cell concentrate, collecting the plasma and reinfusing the cell concentrate into the donor using a disposable tubing or harness set applied to the instrument. Generally, the disposable tubing set may include a venous phlebotomy needle for whole blood collection and blood concentrate reinfusion, a separator for separating anticoagulated whole blood into plasma and cell concentrate, a plasma collection container for receiving the plasma from the separator, a reinfusion reservoir from which cell concentrate flows back to the donor during reinfusion and various tube runs for connection with other parts of the instrument and its various pumps, clamps and detectors. Thus, upon application of the tubing set to the instrument and performing various setup procedures, including venepuncture on the blood donor, the instrument operates to alternate between collection and reinfusion cycles. In the collection cycle, anticoagulated whole blood is pumped by a blood pump to the separator of the tubing set where it is separated into plasma which flows to a collection container and cell concentrate which flows to the reinfusion reservoir. In the reinfusion cycle, the blood pump reverses to flow cell concentrate from the reservoir through the phlebotomy needle to the donor.

Such system is adapted for blood cell separation generally and may be adapted specifically for platelet separation. In general, such systems collect whole blood from the donor, separate off the desired cells, and return the remaining blood components to the donor through a single needle. While a return needle separate from the collection needle can also be used in systems of this general type, for example see U.S. patent application Ser. No. 644,032, filed Aug. 24, 1984, now U.S. Pat. No. 4,776,964, a single venepuncture needle for both collection and reinfusion offers many advantages, including patient comfort and cost minimization. In such systems, the alternate collection and return cycles should be short because it is important not to remove excessive volumes of blood from the donor at any one time.

In accordance with the dual-needle aspect of the present invention, it has been discovered that the magnitude of the driving pressures, during blood processing, to remove whole blood from the vein through one needle and return packed cells to the donor through another needle, varies with time. For example, it has been discovered that, the pressure needed to remove blood from a donor's vein starts out slightly positive and becomes negative until it suddenly returns to a less negative value. While this phenomenon was discovered in a dual-needle system, that is, a system where collection from the donor is accomplished through one needle and reinfusion through another, it is also applicable to single-needle systems. Particularly, it is believed that the phenomena occurs because of a lack of anticoagulant in a first segment of the blood supply line of the tubing or harness set between the single phlebotomy needle (the blood collection needle in a dual-needle system or the single blood collection and reinfusion needle of a single-needle system) and the Y-junction with the anticoagulant line. For example, there is a blood line segment on the order of about twelve inches of tubing between the needle and the Y-junction with the anticoagulant line. It appears that clots form in this tubing segment. Because the clots tend to occlude the tube, the pressure created to maintain a constant flow rate increases to maintain the blood flow constant. Eventually, however, the clot breaks loose and is carried downstream by the blood flow, whereupon the pressure returns to a less negative value. Activation of the blood in this manner is believed to have detrimental effects on both platelet quality and platelet-rich plasma yield. With regard to the latter, activation causes platelet clumping and clumped platelets respond to the centrifugal force in the separator in a manner similar to red cells. Thus, clumped platelets tend to get separated with the red cells and are returned to the donor, thereby reducing platelet yield.

It has therefore been found desirable to avoid or overcome this cause of the variation in pressure in a single-needle hemapheresis system. One way of accomplishing this, according to the present invention, is to prime anticoagulated blood into the reservoir, while simultaneously pumping at a lower rate the contents of the reservoir through the cell separator at a lesser pump rate. Once the reservoir is full, the blood pump is reversed to pump blood from the reservoir for reinfusion into the donor. During reinfusion, however, blood also is pumped from the reservoir to the separation device whereby the separation device continuously separates the blood constituents. In this manner, interruptions in the supply of blood to the reservoir will not affect the platelet separation process. Importantly, clotting tendencies will be diminished in the un-anticoagulated portion of the tubing inasmuch as the blood flow direction in the needle changes rapidly in the course of the collection and reinfusion cycles. Consequently, by frequently reversing the flow of blood through the phlebotomy needle, clot formation is attenuated.

While the foregoing provides a practical solution, it does not take into account the potential problem of mixing unprocessed blood with processed blood. That is to say, the use of a reservoir with a single compartment which is sequentially filled and emptied by a single pump and sampled continuously by another pump for flowing blood to the separation device, necessarily mingles processed and unprocessed blood.

Consequently, and in accordance with another aspect of the present invention, there is provided a single-needle continuous hemapheresis system which provides for substantial isolation of unprocessed blood from processed blood in a single reservoir. This is accomplished by substantially segregating the reservoir of the harness set into two compartments by an internal baffle.

One practical problem arises. It is important that the system which controls the filling and emptying of each reservoir side know precisely how full each one is. Thus, duplication of the number of sensors would be required. This means relatively high costs and complexity. Another approach can be to put undesirable mixing of the two sides of the reservoirs through the through passage can be minimized if the liquid levels in the two sides are kept close to each other. Consequently, a further aspect of the present invention provides for substantial equalization of the flows into and out of the compartments for both unprocessed blood and processed blood in all phases and modes of operation so that the liquid levels remain substantially equal with a minimum of flow through the lower level equalizing port between the compartments. Substantial separation of unprocessed and processed blood is therefore provided.

In accordance with a still further aspect of the present invention, there is provided a tubing or harness set employing a dual-compartment reservoir, similarly as described above, but wherein the fluids in the compartments are completely isolated one from the other except for an overflow port adjacent the top of the reservoir. It must be recognized, however, that the hardware instrumentation for use with this harness set remains the same as in the previously discussed embodiment. In such instrumentation, there are provided, among pumps, clamps, detectors and the like, four sensors vertically superposed one over the other for determining the volume of blood in the reservoir. Where the previously-described system used two compartments with a communicating port at the lower portion of the baffle defining the compartments, such sensors could readily detect various liquid levels in the reservoir. However, when providing two isolated compartments, it was difficult, although highly desirable, to determine the various liquid levels in each compartment using the same instrumentation. That is, these same sensors must determine the fluid level in each of the two compartments in order to properly cycle the instrument. Consequently, the interior baffle dividing the reservoir into the two isolated compartments, in accordance with the present invention, is specifically designed to accommodate and enable use of the sensors of the extant instrument. The baffle is thus formed in a series of lateral offsets or a vertical zigzag shape such that portions of one compartment lie in vertical registry over portions of another compartment and in lateral registry with the sensors. In this manner, two of the four sensors may be used to sense the liquid level in one of the compartments, while the other two sensors may be used to sense liquid levels in the other compartment, all of the sensors lying in vertical registration one with the other.

Accordingly, in accordance with one aspect of the present invention, there is provided apparatus for separating blood received from a donor into constituents, comprising a separator for separating first and second blood constituents from whole blood, a reservoir for containing blood, a single venepuncture needle for supplying whole blood to the reservoir during a whole blood collection cycle and reinfusing blood from the reservoir into the donor during a reinfusion cycle, means for alternately supplying whole blood from the single venepuncture needle into the reservoir during the collection cycle and pumping second blood component from the reservoir to the single venepuncture needle for reinfusing second blood component into the donor during the reinfusion cycle, and means for continuously supplying blood to the separator during the collection and reinfusion cycles, including from the reservoir during the reinfusion cycle, whereby the separator operates continuously to separate the first and second blood constituents from whole blood during alternate collection and reinfusion cycles.

In accordance with another aspect of the present invention, there is provided a hemapheresis apparatus for separating whole blood collected from a donor into first and second blood constituents, comprising a separation device for separating whole blood into the first and second blood constituents, a reservoir having discrete first and second compartments, a single venepuncture needle for drawing whole blood from a donor, a first conduit connecting between the needle and the reservoir for supplying whole blood from the needle to the first compartment of the reservoir during a blood collection cycle, a second conduit connecting between the first compartment and the separation device for supplying whole blood from the first compartment to the separator, an outlet from the separation device for the separated first blood constituent, a third conduit connecting between the separation device and the reservoir for supplying the second blood constituent to the second compartment, and a fourth conduit connecting between the reservoir and the venepuncture needle for returning the second blood constituent from the second compartment through the needle to the donor for reinfusion during a blood reinfusion cycle whereby blood may be alternately collected from a donor in the reservoir and reinfused into the donor from the reservoir while blood is simultaneously and continuously supplied to the reservoir to the separation device.

In a preferred form hereof, the compartments of the reservoir lie side-by-side relative to one another, and a partition wall is carried by the reservoir separating the compartments one from the other for substantial isolation of the unprocessed whole blood and the processed blood for reinfusion. In a particular form of reservoir hereof, the partition wall has portions projecting laterally into the compartments such that the wall portions lie in vertical misalignment one with the other. That is, portions of the wall are laterally staggered relative to one another and located such that portions of said first compartment lie in vertical registration with portions of said second compartment.

In a further aspect of the present invention, there is provided a method for separating first and second blood constituents from whole blood comprising the steps of alternately extracting blood from a donor and reinfusing second blood constituent into the donor while substantially continuously separating the extracted blood into the first and second blood constituents. Preferably, the alternate steps of extracting and reinfusing blood are performed through a single needle.

In a still further embodiment of the present invention, there is provided a method of avoiding clot formation in an un-anticoagulated tubing portion of a hemapheresis tubing set having a single venepuncture needle, the tubing portion being disposed between a connection for supplying anticoagulant to the tubing set and the needle comprising the steps of collecting blood from the donor through the tubing portion, reinfusing blood into the donor through the tubing portion, and alternately collecting and reinfusing blood through the tubing portion within a period of time sufficient to substantially avoid clot formation in such un-anticoagulated tubing portion.

Thus, it is a primary object of the present invention to provide novel and improved hemapheresis apparatus and methods for continuously separating blood constituents from whole blood while alternating blood collection and reinfusion cycles, preferably in a single-needle system, and precluding clot formation in un-anticoagulated portions of the whole blood conduit.

These and further object and advantages of the present invention will become more apparent upon reference to the following specification, appended claims and drawings.

DETAILED DESCRIPTION OF THE DRAWING FIGURES

FIGS. 3 and 4 are side and front cross-sectional views of the reservoir used in the harness set applied to the instrument of FIG. 2;

FIG. 7 is a perspective view with parts broken out and in cross-section of the reservoir used in the harness set illustrated in FIG. 6; and FIG. 8 is an enlarged fragmentary longitudinal cross-sectional view through the reservoir illustrated in FIG. 7.

DETAILED DESCRIPTION OF A PREFERRED EMBODIMENT

Reference will now be made in detail to the present preferred embodiment of the invention, an example of which is illustrated in the accompanying drawings.

Figure 1:
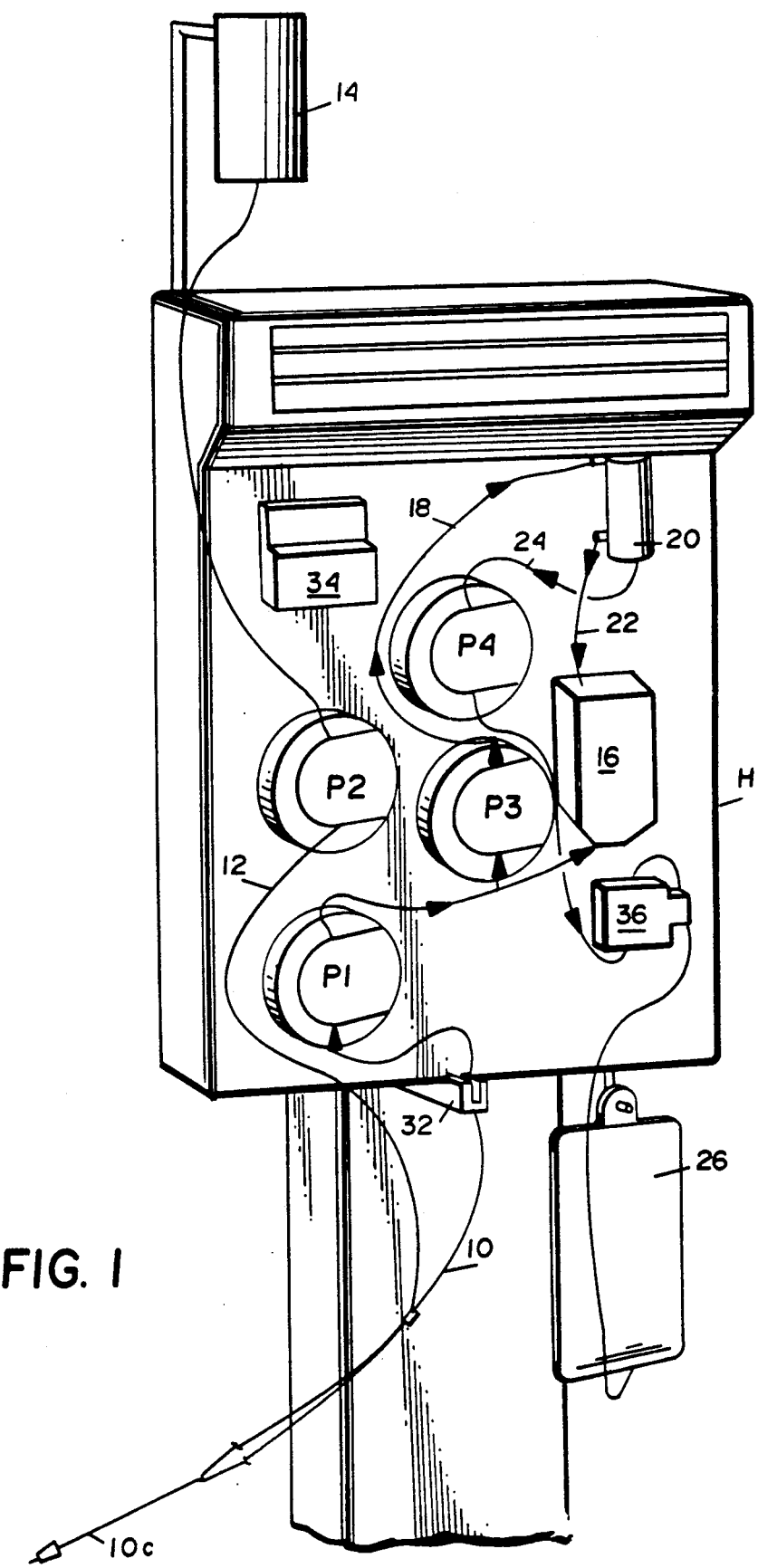
FIG. 1 is a perspective view of a hemapheresis instrument with a harness set constructed in accordance with the present invention and applied to the instrument.

Referring now to FIG. 1, there is illustrated a hemapheresis system for use in practicing one aspect of the present invention. In this system, there is provided a tubing or harness set for application to the hemapheresis instrument H. The harness set includes a venepuncture needle set, not shown, comprised of a single needle for receiving whole blood from a donor and reinfusing a separated second component into the donor. The venepuncture needle set communicates with a blood line 10. An anticoagulant line 12 joins blood line 10 adjacent the venepuncture needle set through a Y-connection. Anticoagulant line 12 communicates with an anticoagulant supply 14 through suitable connections. It will be appreciated that there is a distance of blood line tubing 10 (10C) between the needle set and the Y-connection with the anticoagulant line 12 in which whole blood flows without anticoagulant. It is this length of tubing in which the clots may form, as previously discussed.

The tubing or harness set also includes a reservoir 16 and a branch conduit 18 which communicates anticoagulated whole blood in blood line 10 into a blood component separator 20, also forming part of the harness. A conduit 22 communicates between separator 20 and reservoir 16 for directing the separated second component into reservoir 16. A conduit 24 communicates between the lower end of separator 20 and a separated primary component collection bag 26. It will be appreciated that the aforedescribed tubing set or harness is manufactured and sold as a disposable for application to a hemapheresis instrument which, when operated in conjunction with the applied tubing set, performs the collection, reinfusion and separating functions.

The hemapheresis system hereof comprises both the harness set and the instrument. Generally, the system, with the harness set applied, requires a single venepuncture and alternates between collection of whole blood and reinfusion of residual concentrate while continuously separating whole blood into constituents using a system of pumps, clamps and sensors controlled by a microprocessor. Particularly, instrument H includes a plurality of pumps to which the harness set is applied to pump the various fluids. For example, blood line or tubing 10 is applied to a pump P1 for pumping blood to and from the donor to reservoir 16. The anticoagulant line 12 is applied to pump P2 for pumping anticoagulant from supply container 14 through anticoagulant line 12 into blood line 10 adjacent the venepuncture needle. Tubing 18 is applied to a pump P3 connecting between blood line 10 and an inlet port to separator 20. Tubing 24 is applied to pump P4 for pumping the desired separated component from separator 20 to the collection bag 26. Pumps P1, P2, P3 and P4 are preferably of a peristaltic type. It will be appreciated that there are various other detection devices and other features provided on the face of the instrument, for example, an air detector 32 for detecting air in the blood line, a pressure transducer assembly 34, which is coupled to the harness, by means not shown, a hemoglobin detector 36 and other sensors and clamps, all of which need not be described herein for an understanding of the present invention.

The operation of instrument H is under the control of a microprocessor. In use, the harness set is applied to the instrument and various checks are made by the instrument and the phlebotomist to ensure that the instrument is functioning properly. Venepuncture is then performed and pump P2 is actuated. Pump P2 pumps anticoagulant from supply 14 through line 12 into the blood line immediately behind the venepuncture needle. Pump P1 is also activated to pump anticoagulated blood through line 10 into reservoir 16 to prime the latter. At the same time, pump P3 is actuated to pump blood from blood line 10 into separator 20. It will be appreciated that, according to the present invention, the volumetric flow pumped by pump P3 through line 18 to separator 20 is less than the volumetric flow of anticoagulated blood in line 10. Therefore, reservoir 16 will eventually fill with anticoagulated blood. Pump P4 is also actuated to pump the desired blood component product separated from anticoagulated whole blood by separator 20 for delivery through line 24 to collection bag 26. Consequently, it will be appreciated that blood is collected from the donor and simultaneously separated by separator 20. The separated blood product from separator 20 flows continuously into reservoir 16 via line 22. Thus, during this collection and separation stage, reservoir 16 is being filled by the portion of the donor's blood not pumped into separator 20 through line 18 as well as by the residual blood components, i.e., red cells and white cells, exiting separator 20 via line 22.

Once the reservoir has filled, an optical sensor, not shown, on the instrument, senses the level of blood in the reservoir and, in response thereto, the microprocessor reverses the direction of blood pump P1. This initiates the reinfusion cycle, whereby blood is pumped from reservoir 16 through blood line 10 by pump P1 for reinfusion into the donor through the single venepuncture needle. Simultaneously and continuously therewith, blood is pumped from line 10 by pump P3 for delivery through line 18 to separator 20. At the same time, residual blood flows from separator 20 into reservoir 16. Consequently, reservoir 16 is drained of blood by pump P1 during reinfusion and by pump P3 which delivers blood to separator 20. Simultaneously, residual blood flows into reservoir 16 via line 22. Consequently, reservoir 16 empties. When the reservoir is close to being completely emptied, a sensor, not shown, senses the level of fluid in the reservoir and, in response, the microprocessor once again reverses pump P1, whereupon the instrument repeats the previously described collection cycle. Thus, during both collection and reinfusion stages, separator 20 operates continuously to effect separation.

By operating the system of the present invention in this manner, the collection/reinfusion cycles are alternated relatively rapidly, i.e., within a few minute's time. By effecting rapid alternate collection and reinfusion cycles, the un-anticoagulated portion of tubing 10 between the venepuncture needle and the Y-connection with the anticoagulant line 12 is rapidly back-flushed with anticoagulated blood and in sufficient time to preclude clot formation in that portion of the blood line. Consequently, the abrupt pressure changes discovered, as previously mentioned, are eliminated and the potentially adverse effects of such pressure changes on the blood including clotting are likewise eliminated.

Turning now to the embodiment of the present invention illustrated in FIGS. 2-5, there is illustrated apparatus for substantially isolating unprocessed and processed blood in a single reservoir. This is accomplished by providing an internal baffle in the reservoir to divide it into two discrete compartments except for a bypass port at the bottom of the baffle and by control of input processed and unprocessed blood to the reservoir whereby liquid levels in the compartments of the reservoir are equalized and substantial isolation between unprocessed blood and processed blood is maintained. In the previous embodiment, it will be appreciated that the processed and unprocessed blood were mixed in a single reservoir. It has been found desirable, however, to maintain such processed and unprocessed bloods substantially segregated. However, the existing hemapheresis instrument imposes certain constraints on the design of a system for maintaining processed and unprocessed bloods segregated in a single reservoir. For example, it is necessary to determine the volume of blood in the two compartments of the reservoir which store processed and unprocessed blood, respectively. Therefore, while it is considered desirable to maintain the processed and unprocessed blood segregated, any such system for segregating the blood has to be compatible with the instrument and particularly with the sensors extant on the instrument for determining liquid level in the previously single compartmented reservoir. According to this embodiment of the invention, two substantially separate compartments are provided in the reservoir and constant liquid levels are maintained by providing for control of the flow into and out of the two compartments, thereby eliminating or minimizing significant flow from one compartment to the other through the bypass port, and enabling blood level sensing to be accomplished by sensors provided on an existing instrument.

Figure 2:
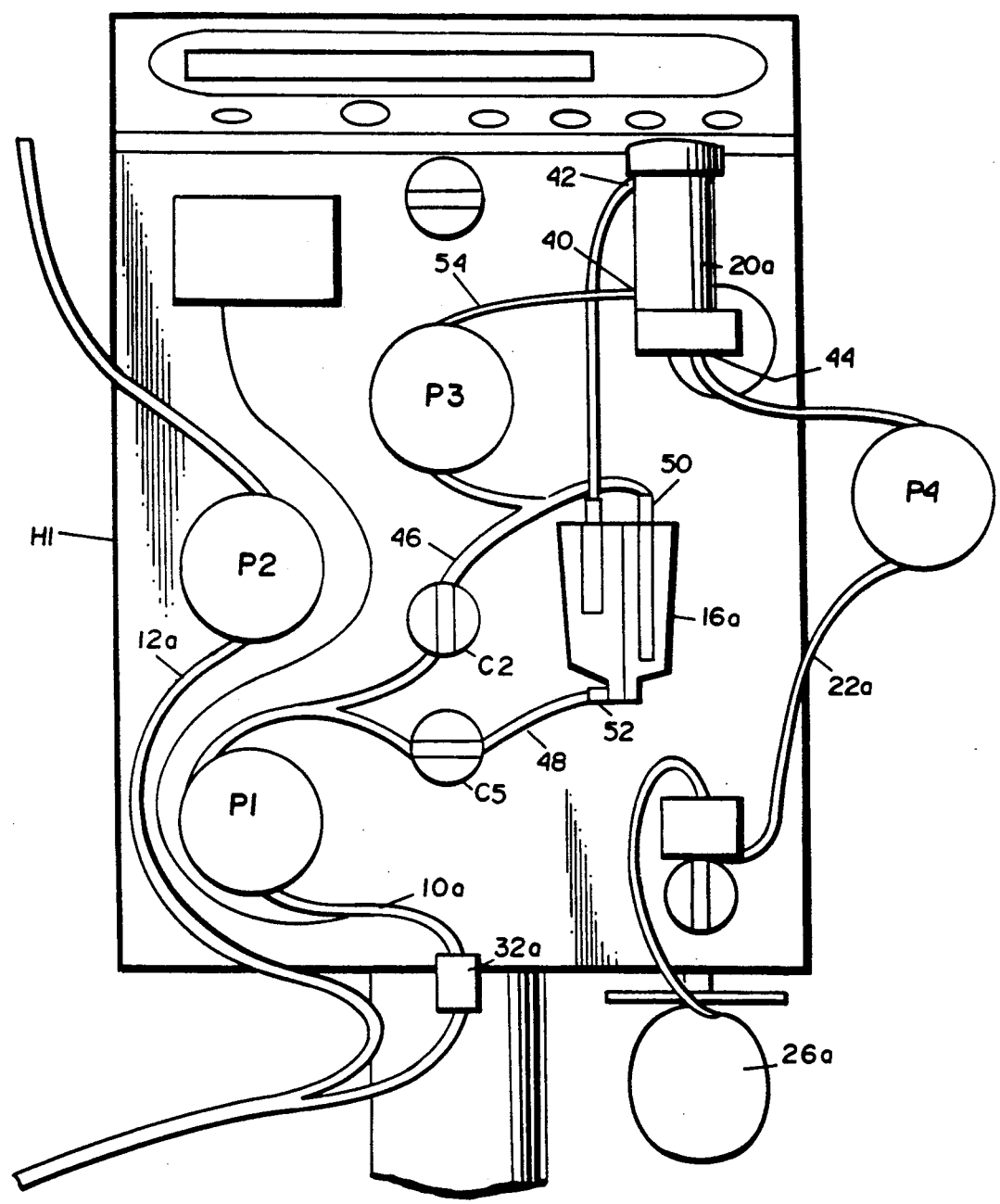
FIG. 2 is a front elevational view of another form of instrument and harness set applied thereto constructed in accordance with the present invention.

Accordingly, in FIG. 2, there is illustrated an instrument H1 substantially similar to the instrument H described previously. Here, motor P4 is disposed to one side of the instrument rather than on its face. Also, clamps C2 and C5 are provided. The tubing or harness set is also somewhat differently arranged and includes a platelet separator 20a, for example, as described and illustrated in U.S. patent application Ser. No. 644,032. That separator, for example, has three ports, a blood inlet port 40, packed blood cell port 42 and a platelet-rich plasma port 44. Additionally, blood line 10a has a pair of branch lines 46 and 48 which extend through clamps C2 and C5, respectively, when the harness set is applied to the instrument. Line 46 extends for connection to a draw tube 48 disposed in a reservoir 16a, to be described. Line 48 connects with an inlet port 52 at the lower end of reservoir 16a. Additionally, a line 54 communicates with line 46 between draw tube 50 and clamp C2 and is connected at its opposite end to inlet port 40 of separator 20a.

Referring now to FIGS. 3 and 4, the reservoir 16a of the harness set illustrated in FIG. 2 will now be described. Reservoir 16a comprises a housing 60 having side, front and back walls, a top wall and a tapered lower wall terminating in a downwardly extending central channel 62. Reservoir 16a is divided into separate, side-by-side compartments 64 and 66 by a baffle 68, which extends between the top wall and into channel 62. From a review of FIGS. 3 and 4, it will be appreciated that baffle 68 substantially isolates compartments 64 and 66 one from the other, except for a lower cutout 70 along the lower rear side of baffle 68 and a cutout 72 along the upper rear side of baffle 68. Cutout 70 forms with the side and bottom walls of the reservoir 16a a bypass port 74 providing communication between chambers 64 and 66. Cutout 72 at the upper end of the baffle provides, in conjunction with the back wall of reservoir 16a, an overflow passage 76. The rear wall of the reservoir has a rearwardly extending channel 78, which is received in a portion of the instrument face for purposes of measuring fluid levels. Card readers are provided on the front panel of the instrument and their locations are designated by the identifying characters S1, RS1, S2 and RS2 and the levels thereof which are sensed are indicated by the dashed lines in FIGS. 4.

Referring back to FIG. 2, the flow paths of the blood through the harness set when applied to the instrument H1 will now be described with respect to the various stages of operation. Once the harness has been applied to instrument H1, and all checks have been performed by the instrument and operator, the instrument enters a first priming mode. In this mode, anticoagulant pump P2 is activated to provide anticoagulant through anticoagulant line 12a into blood line 10a. Pump P1 is activated, clamp C2 is closed and clamp C5 is opened, whereby anticoagulated blood is provided through blood line 10a into the lower portion of reservoir 16a up to a level S1. In this initial prime, the blood communicates through bypass port 74 with both chambers 64 and 66, whereby the level in both chambers is substantially constant. After the reservoir prime, the separation device is primed. To accomplish this, clamp C5 is closed and clamp C2 is opened and all pumps P1–P4 are activated. Anticoagulated blood therefore flows through blood line 10a for delivery into reservoir 16a, particularly compartment 66 through draw tube 50. A portion of the anticoagulated blood delivered through line 10a is pumped by pump P3 through line 54 for delivery to separation device 20a through inlet port 40. Platelet-rich plasma is delivered from separator 20a through exit port 44 and pumped by pump P4 into collection bag 26a. Packed cells are delivered via line 53 into reservoir 16a, particularly compartment 64. Consequently, the filter of separating device 20a is primed while anticoagulated, unprocessed whole blood is delivered compartment 66 via line 46 and processed blood is delivered compartment 64 via line 53. Once the filter is primed, the system, under the control of the microprocessor, commences its blood collection cycle.

In this cycle, anticoagulated blood is delivered via blood line 10a to compartment 66 of reservoir 16a via line 46 and also separator 20a via line 54 and inlet port 40. It will be appreciated that the harness may be constructed such that the whole blood from the donor may be supplied in its entirety to the reservoir and then from the reservoir to the separator rather than being supplied in part directly to the separator from the donor and in the remaining part directly to the reservoir compartment from the donor. Packed cells flow via line 53 from separator 20a into compartment 64 of reservoir 16a while platelet-rich plasma flows into collection bag 26a via line 22a. In this collection cycle, the pump rates are set such that substantially equal flows are provided the two compartments 64 and 66 of reservoir 16a via the packed cells return line 53 and blood supply line 46. It should be noted that the blood supply pump rate, i.e., pump P3, and the processed flow rate through line 53. That is, the blood pump rate is equal to the supply pump rate×2 minus the concentrate pump rate. Vein conditions causing regulation of the blood pump can be accommodated by either slowing all pumps or sacrificing some mixing of unprocessed and processed blood in the reservoir or a combination of the two. It is advantageous to make the lower level equalizing port 74 quite small so that any mixing is delayed for variations such as vein regulation or variations in concentrate flow which will occur during red-spill occurrences.

The reservoir eventually becomes full due to the influx of both processed blood and unprocessed blood through lines 53 and 46, respectively. At this stage, a reinfusion cycle is initiated. That is, the blood levels in both compartments 64 and 66 have reached the level S2 indicated in FIG. 4 and the instrument sensor detects such levels. The microprocessor responds by controlling the instrument to initiate a reinfusion cycle.

To start the reinfusion cycle, the microprocessor controlled instrument causes clamp C2 to close and clamp C5 to open. Blood pump P1 is reversed and blood is drawn from the bottom of reservoir 16a for delivery via branch line 48 and blood line 10a to the single venepuncture needle for P3 is maintained activated to pump blood from compartment 66 via line 54 to separator 20a. Platelet-rich plasma pump P4 is also maintained activated to flow platelet concentrate from separator 20a via line 22a into collection bag 26a. The outflow of blood from reservoir 16a via the blood lines 48 and 10a is taken substantially from compartment 64, which is being continuously supplied with processed blood via line 53. Simultaneously, blood is being removed from compartment 66 via line 54 for delivery to the separator 20a. The blood pump (rates are adjusted such that the outflow from compartment 64 via blood line 48 and 10a, less the input to compartment 64 via line 53, is equal to the output via line 54 from blood compartment 66. In this manner, the levels of the processed and unprocessed blood in compartments 64 and 66, respectively, are maintained substantially equal as the overall level of the liquid in reservoir 16a decreases. It is important to note that this equalization of the flow does not cause substantial flow through bypass port 74 and therefore the processed and unprocessed bloods in the compartments 64 and 66 will not be substantially intermingled.

When the blood level reaches the level indicated RS1 in FIG. 3, that low level is sensed and the microprocessor responds by indicating an end reinfusion stage. At this stage, it is necessary to stop blood pump P1 quickly, pressurize the cuff on the donor, obtain a vein control zero flow point, reverse blood pump P1 and return processed blood in the tubing into the reservoir before supply pump P3 draws air through the bottom of draw tube 50. To accomplish this, supply pump P3 is slowed along with pump P4 to reduce or stop the flow of platelet-rich plasma. The separator may also be slowed at this time.

Once the pressure cuff has been inflated and the blood pump is reversed, processed blood is returned to the reservoir from the tube set. To accomplish this, the blood pump P1 is reversed to flow blood via lines 10a and 48 into the lower part of the reservoir 16a. The supply flow through line 54 is held at a low rate and platelets are not collected. At the end of this process, the collection cycle begins and the pumps and clamps are operated as previously discussed.

Figure 5:
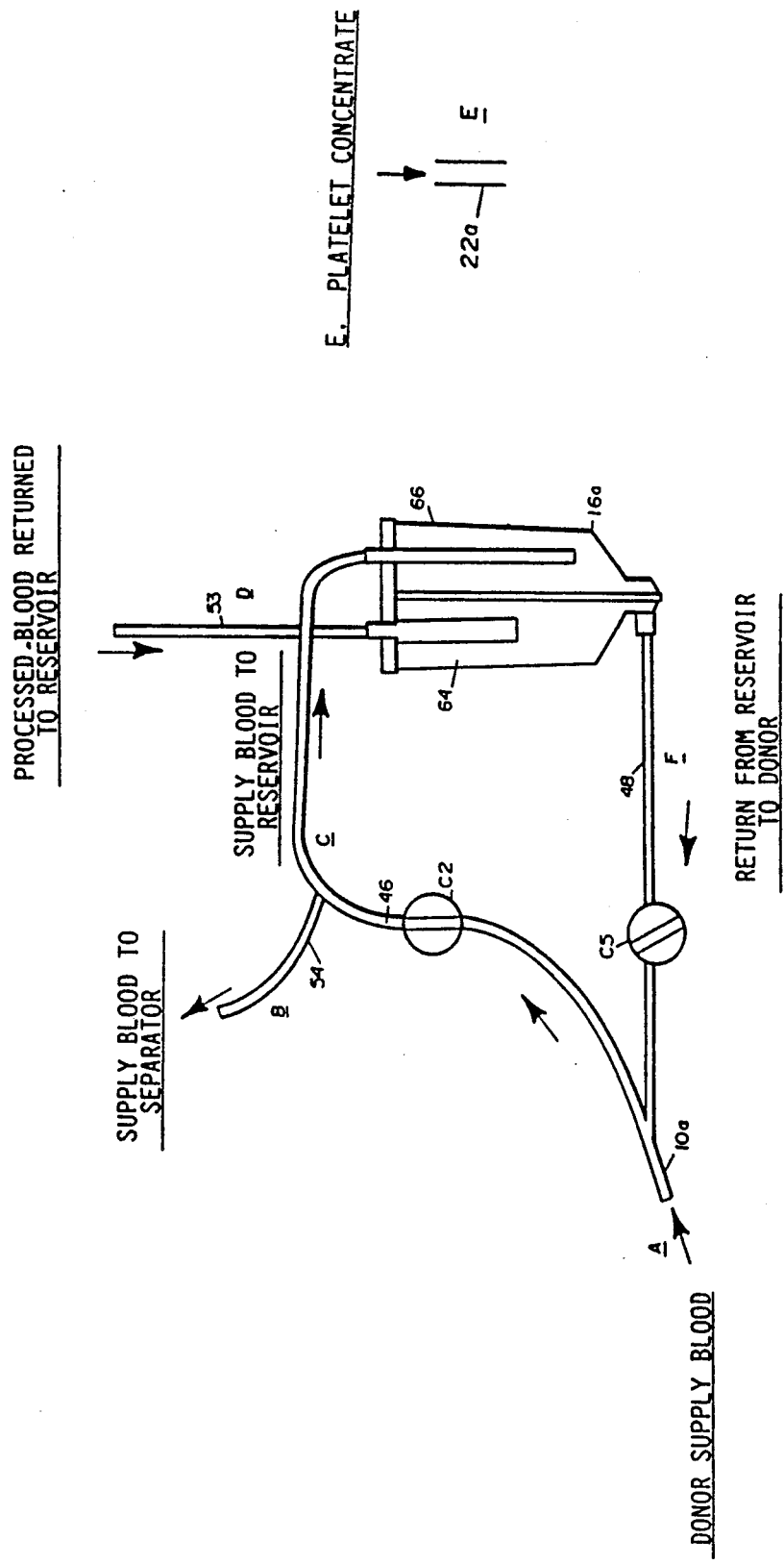
FIG. 5 is a schematic view of portions of the harness set applied to the instrument of FIG. 2.

A chart of representative exemplary flow rates at various locations in the system is set forth below in connection with FIG. 5. The flows are given in terms of ml/min. The lefthand column of the chart below identifies the stage of the process, while the remaining column headings identify the various locations in the system. Thus, the blood flow rate at each relevant location is given for each stage of the process. The headings of these charts identify the location in the system of the flow charts by corresponding letter reference A–F as applicable in drawing FIG. 5. The negative signs indicate the reverse flow from that indicated by the column heading for that location and the corresponding stage.

| | REPRESENTATIVE SYSTEM FLOW RATES FOR EACH RELEVANT LOCATION AND SYSTEM STAGE | | | | | |
| --- | --- | --- | --- | --- | --- | --- |
| | A From Donor | B Supply to Separator | C To Blood Res. | D Proc. Blood Into Res. | E Donor to Res. | F Platelet-Rich Plasma Flow |
| 1st Priming Mode | 50 | 0 | 0 | 0 | +50 | 0 |
| Separation Prime | 70 | 50 | 20 | 50 | 0 | 0 |
| Extraction | 90 | 50 | 40 | 40 | 0 | 10 |

-continued

REPRESENTATIVE SYSTEM FLOW RATES FOR
EACH RELEVANT LOCATION AND SYSTEM STAGE

|  | A<br>From Donor | B<br>Supply to<br>Separator | C<br>To Blood Res. | D<br>Proc. Blood<br>Into Res. | F<br>Donor to Res. | F<br>Platelet-Rich<br>Plasma Flow |
| --- | --- | --- | --- | --- | --- | --- |
| (Res. Being Filled) |  |  |  |  |  |  |
| Reinfusion | −90 | 50 | −50 | 40 | −90 | 10 |
| End Reinfusion | 0 | 30 | −30 | 30 | 0 | 0 |
| Process Blood | +50 | 30 | −30 | 30 | +50 | 0 |
| Return Into Reservoir |  |  |  |  |  |  |
| Start Extraction | 90 | 50 | 40 | 40 | 0 | 10 |
| Cycle |  |  |  |  |  |  |

Thus, for example, during the extraction cycle, whole blood flows at a rate of 90 ml/min. through blood line 10a; 50 ml/min. flow through line 54 to separator 20a; 40 ml/min. flow through line 46 into reservoir compartment 66; 40 ml/min. flow from separator port 42 of separator 20a into compartment 64 of reservoir 16a; 10 ml/min. flow from outlet port 44 of separator 20a via line 22a into collection bag 26a and 0 ml/min. flow from reservoir 16a back to the donor.

As will be appreciated, both compartments 64 and 66 empty at substantially the same rate, as well as fill at substantially the same rate. However, pump flow rate errors caused by tubing diameter, tension and input pressure to the blood pump and the supply pump will cause some mixing of processed and unprocessed blood in the first cycle. During that cycle, the known volume from RS1 to RS2, the measured pump motions, and the measured difference observed by the measure of flow through the concentrate pump enables relative calibration for later cycles. Additionally, in the first cycle, the unprocessed blood could intentionally be increased over the processed blood into the reservoir, if necessary, to bias the errors in one direction. Controlled tubing within the pumps and possibly tube stops added to the supply pump P3 would further decrease any errors in that system.

Figure 6:
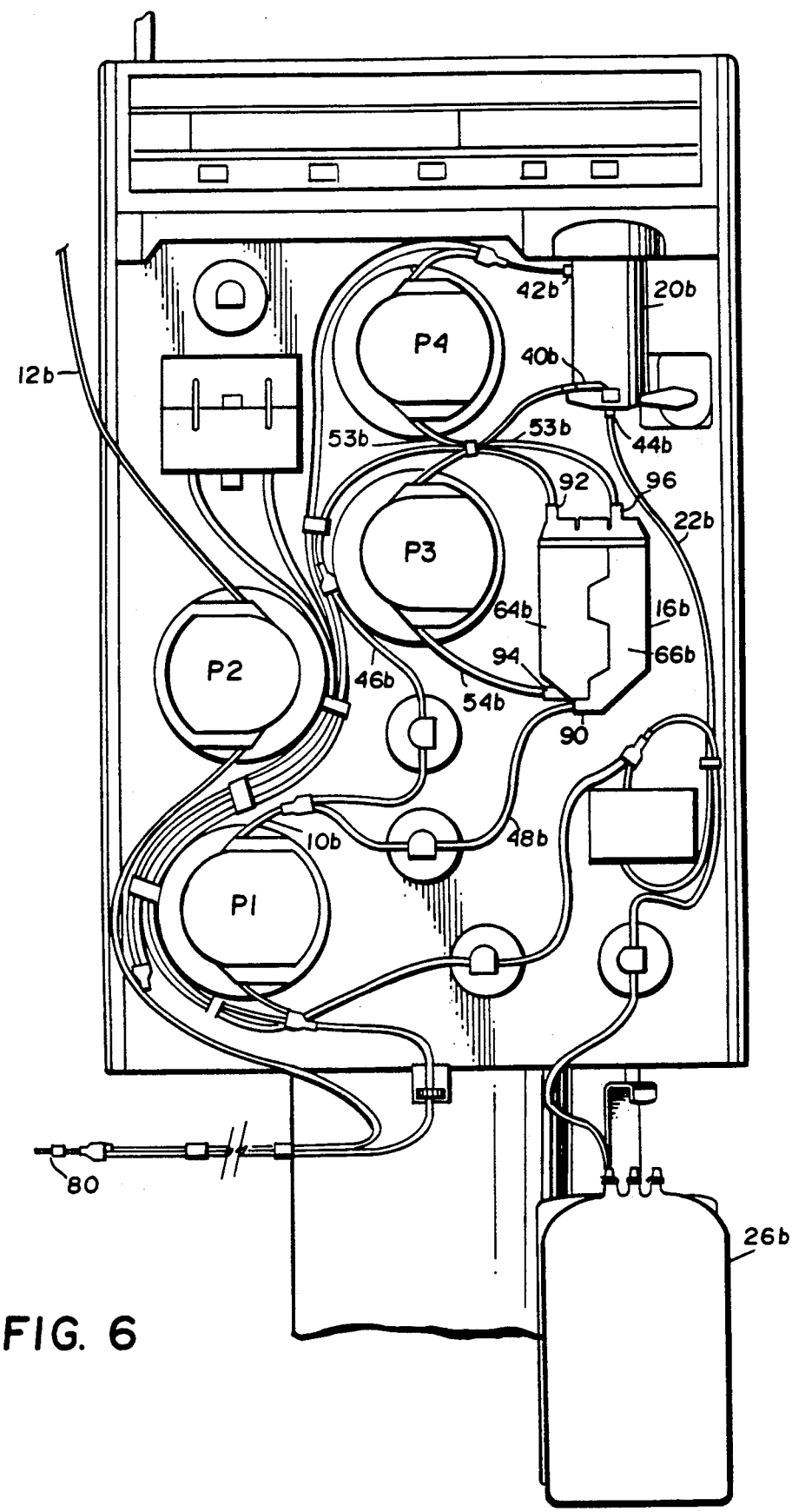
FIG. 6 is a still further embodiment of an instrument and harness set applied thereto constructed in accordance with the present invention.

Turning now to the embodiment hereof illustrated in FIGS. 6-8, there is illustrated a system wherein the compartments of the reservoir are completely isolated one from the other, except for an overfill passage at the top of the reservoir. Moreover, this isolation is accomplished within the constraints of the locations of the liquid level sensors in the existing instrument. This necessitates a slightly different harness set for installation on the instrument as will now be described.

The harness set for use with this embodiment of the invention includes a blood line 10b connected with a venepuncture needle designated 80. Blood line 10b branches into lines 48b and 46b. Branch line 48b is coupled to blood line 10b through a Y-connection and to a lower outlet port 90 of reservoir 16b. Branch line 46b connects with the Y-connection with blood line 10b and an inlet port 92 for reservoir 16b. A line 54b connects between an outlet port 94 of reservoir 16b and an inlet port 40b of separator 20b. A line 53b connects between the inlet port 96 of reservoir 16b and the outlet port 42b of separator 20b. A line 22b connects between the outlet port 44b of separator 20b and with a collection bag 26b.

Referring now to FIGS. 7 and 8, the reservoir 16b is segregated into two discrete compartments 64b and 66b with a baffle 68b separating the compartments one from the other. The baffle forms an integral portion of the housing for the reservoir and provides for complete isolation of compartments 66b and 68b one from the other. Thus, whole blood compartment 64b has inlet port 92 and outlet port 94, while packed cell compartment 66b has inlet port 96 and outlet port 90 at its bottom. Draw tubes, now shown, are provided in communication with each of inlet ports 92 and 96, respectively, and extend into the respective compartments.

It is a particular feature of the present invention that the dual-compartment reservoir is specifically adapted for use with the sensors on the instrument face. As will be recalled, liquid levels in the reservoir are detected and signals generated thereby control the operation of the system. The reservoir illustrated in FIGS. 7 and 8 is specifically adapted to use those very same sensors but in a manner to effectively sense the liquid level in each of compartments 64b and 66b. To adapt the reservoir to the existing locations of the sensors, i.e., in vertical alignment one over the other, the baffle 68b has a zigzag or laterally offset cross-sections. That is to say, the baffle is comprised of laterally offset vertical portions interconnected by laterally extending portions. In this way, when the reservoir is applied to the instrument, the sensors RS2 and RS1 may be used to sense the liquid levels in compartment 64b, while the sensors S1 and S2 may be used to sense the liquid level in compartment 66b. Note that the position of the sensors is not changed.

The harness set described above is applied to the instrument by inserting the reservoir 16b in a mount, not shown, applying line 10b to pump P1, lines 46b and 48b to clamps C2 and C5, respectively, line 54b through pump P3 and line 53b through pump P4. As in previous embodiments, the anticoagulant line 12b is applied to pump P2.

In using this system, and after the donor has been connected to the phlebotomy needle 80, system checks have been made and the reservoir and separator are primed, anticoagulated blood is pumped by pump P1 through line 10a and branch line 46b past opened clamp C2 into reservoir compartment 64b via inlet port 92. Anticoagulated blood is pumped by pump P3 through line 54b and inlet port 40b into separator 20b. Packed cells from separator 20b are pumped by pump P4 through outlet 42b and via line 53b into reservoir compartment 66b. Platelet-rich plasma is delivered from outlet 44b of separator 20b through line 22b to collection bag 26b. It will be appreciated that during this collection cycle, only a portion of the whole blood volume delivered to compartment 64b is delivered to separator 20b. Simultaneously, only a portion of the whole blood volume delivered to the separator is returned to the reservoir in compartment 66b as the remaining portion is collected in bag 26b. Consequently, the liquid levels in both compartments will rise, while maintaining complete separation of the liquid input into the compartments.

When the liquid levels reach predetermined levels and are sensed, the microprocessor responds by starting the reinfusion cycle. Consequently, clamp C2 is closed and clamp C5 is opened. Pump P1 is reversed and packed cells are pumped from compartment 66b through branch line 48b, past open clamp C5 and through line 10a for reinfusion into the donor through venepuncture needle 80. Pump P3, however, continues to deliver whole blood from compartment 64b via line 54b to the separator 20b. Thus, during both collection and reinfusion cycles, separator 20b operates continuously to maintain an output of platelet-rich plasma. When the liquid levels in the reservoir compartments are again sensed prior to complete depletion of the liquids in the compartments, the microprocessor responds to initiate the collection cycle. Thus, clamp C5 is closed and clamp C2 is opened. Pump P1 is again reversed to provide anticoagulated blood into whole blood compartment 64b via lines 10b and 46b. Packed cells from separator 20b are pumped by pump P4 into the compartment 66b via lines 53b. Consequently, both compartments are being filled with the respective blood fluids.

Advantageously, the packed cells and whole blood are maintained separated continuously while the cycle times remain short, precluding the clotting problem previously noted with respect to the first unanticoagulated tube portion between the venepuncture needle and the Y-connection with the anticoagulant line. Additionally, the discontinuous collection and reinfusion cycles enable use of a single venepuncture needle and its attendant advantages.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A harness set for a hemapheresis instrument comprising:
   a separation device for processing blood fluid;
   a housing defining a reservoir having discrete first and a second compartments separated by a partition wall and including means on the wall defining a port for establishing communication between the two compartments, the reservoir having first and second outlet ports generally located at the lower end of the first and second compartments, respectively, as well as first and second inlet ports generally located at the upper ends of the first and second compartments, respectively;
   a venepuncture needle;
   first means for establishing blood fluid communication between said needle and the first inlet port located in said first compartment of said reservoir;
   second means for establishing blood fluid communication between the first outlet port located in said first compartment of said reservoir and said separator;
   third means for establishing blood fluid communication between said separator and the second inlet port located in said second compartment of said reservoir; and
   fourth means for establishing blood fluid communication between the second outlet port located in said second compartment and said venepuncture needle, whereby blood fluid may be collected from a donor in the first reservoir compartment and returned to the needle from the second reservoir compartment while blood fluid is simultaneously and continuously supplied from said first reservoir compartment to said separation device.

2. Apparatus according to claim 1 wherein said partition wall has portions projecting laterally into said compartments such that said wall portions lie in vertical misalignment one with the other.

3. Apparatus according to claim 2 wherein said misaligned portions of said partition wall are laterally staggered relative to one another and located such that portions of said first compartment lie in vertical registration with portions of said second compartment.

4. A harness set according to claim 1
   wherein the compartments lie side-by-side and the port is located in a lower portion of the partition wall.

5. A method for separating first and second blood constituents from whole blood received through a single venepuncture needle connected to a donor, comprising the steps of:
   alternately supplying whole blood from the donor through the needle to a reservoir during a blood collection cycle and supplying blood from the reservoir through the needle for reinfusion into the donor during a blood reinfusion cycle;
   continuously supplying blood to a separator during both collection and reinfusion cycles;
   continuously separating the whole blood into first and second blood constituents during both collection and reinfusion cycles to continuously provide the first blood constituent; and
   continuously supplying the second blood constituent from the separator to the reservoir during both the collection and reinfusion cycles, and
   wherein the reservoir has a pair of compartments, and including the steps of supplying whole blood from the donor to an inlet located generally at the upper portion of the first compartment during the collection cycle, continuously supplying the second constituent from the separator to an inlet located generally at the upper portion of the second compartment during both the collection and reinfusion cycles, and supplying the second constituent from an outlet located generally at the lower portion of the second compartment to the needle for infusion into the donor during the reinfusion cycle.

6. A method according to claim 5 including providing communication between said compartments.

7. A method according to claim 6 including isolating said compartments one from the other to preclude intermingling of whole blood and the second constituent.

8. A method according to claim 5 including, during the collection cycle, supplying blood to the separator at a rate substantially equal to the rate at which blood is supplied from the donor less the rates at which the second blood constituent is supplied to the reservoir.

9. A method according to claim 5 including, during the collection cycle, the steps of supplying blood to the first compartment at a rate substantially equal to the rate at which the second blood constituent is supplied to the second compartment whereby the blood levels in said compartments remain at substantially like levels.

10. A method according to claim 5 including the steps of providing said first and second compartments of a size to maintain substantially the same blood levels therein during both collection and reinfusion cycles.

11. A method according to claim 5 including, during the reinfusion cycle, the steps of supplying blood from said first compartment to said separator at a rate substantially equal to the rate the second blood constituent is supplied from said second compartment for reinfusion to the donor less the rate the second blood constituent is supplied to said second compartment from said separator.

12. A method of avoiding clot formation in an unanticoagulated tubing portion of a hemapheresis tubing set having a single venepuncture needle, the tubing portion being disposed between a connection or supplying anticoagulant to the tubing set and the needle comprising the steps of:
   collecting blood from the donor through the tubing portion;
   reinfusing blood into the donor through the tubing portion; and
   alternately collecting and reinfusing blood through the tubing portion within a period of time sufficient to substantially avoid clot formation in such unanticoagulated tubing portion.

13. A method according to claim 12 wherein said period of time is about one minute.

14. A method according to claim 12 wherein said period of time is no greater than three minutes.

15. Apparatus for separating blood received from a donor into constituents, comprising:
   a separator for separating first and second blood constituents from whole blood;
   a reservoir for containing blood;
   a single venepuncture needle for supplying whole blood to the reservoir during a while blood collection cycle and reinfusing blood from the reservoir into the donor during a reinfusion cycle;
   means for alternately supplying whole blood from the single venepuncture needle into the reservoir during said collection cycle and pumping blood from the reservoir to the single venepuncture needle for reinfusing blood into the donor during said reinfusion cycle; and
   means for continuously supplying blood to said separator during the collection and reinfusion cycles including from said reservoir during said reinfusion cycle whereby said separator operates continuously to separate the first and second blood constituents from whole blood during alternating collection and reinfusion cycles, said reservoir having a pair of compartments, said alternate supply means including a first conduit for supplying whole blood to one of said compartments during the collection cycle, said continuous supplying means including a second conduit for supplying whole blood from said first conduit to said separator during the collection cycle, a third conduit for supplying blood from the separator to the second compartment, said alternate supplying means including a fourth conduit for supplying blood from said second compartment to said needle during the reinfusion cycle.

16. Apparatus for separating blood received from a donor into constituents, comprising:
   a separator for separating first and second blood constituents from whole blood;
   a reservoir for containing blood;
   a single venepuncture needle for supplying whole blood to the reservoir during a whole blood collection cycle and reinfusing blood from the reservoir into the donor during a reinfusion cycle;
   means for alternately supplying whole blood from the single venepuncture needle into the reservoir during said collection cycle and pumping blood from the reservoir to the single venepuncture needle for infusing blood into the donor during said reinfusion cycle; and
   means for continuously supplying blood to said separator during the collection and reinfusion cycles including from said reservoir during said reinfusion cycle whereby said separator operates continuously to separate the first and second blood constituents from whole blood during alternating collection and reinfusion cycles, said reservoir having a pair of compartments, said alternate supplying means including a first conduit for supplying whole blood to one of said compartments during the collection cycle, said continuous supplying means including a second conduit for supplying whole blood from said one compartment to said separator during the collection cycle, a third conduit for supplying blood from the separator to the second compartment, said alternate supplying means including a fourth conduit for supplying blood from said from second compartment to said needle during the reinfusion cycle.

17. A system for separating whole blood into its constituents comprising
   a single venepuncture needle,
   separation means for separating at least one constituent from whole blood,
   a reservoir,
   conduit means interconnecting the needle, the separation means, and the reservoir and being operative in a first mode for withdrawing whole blood from the donor through the needle and for collecting a quantity of the withdrawn blood in the reservoir while conveying another quantity of the withdrawn whole blood to the separation means in a path that bypasses the reservoir, the conduit means being further operative in a second mode for returning a separating constituent of the whole blood from the separation means to the donor through the needle while conveying blood from the reservoir to the separation means,
   means for alternating operation of the conduit means between the first and second modes to withdraw whole blood and then return a separated constituent while continuously supplying blood to the separation means.

18. A system according to claim 17 wherein the conduit means includes means for collecting the separated constituent for return to the donor.

19. A system according to claim 18 wherein the separated constituent collection means comprises the reservoir where whole blood is also collected when the conduit means is operated in the first mode.

20. A system according to claim 18 wherein the separated constituent collection means comprises a second reservoir.

21. A system according to claim 17 wherein, in the second mode of operation, the conduit means conveys whole blood to the separation means substantially free of mixing with the returned constituent.

22. A system according to claim 17 wherein the conduit means includes
- first conduit means between the needle and the reservoir for conveying the quantity of withdrawn whole blood to the reservoir, and
- bypass conduit means between the first conduit means and the separation means for conveying the other quantity of whole blood from the first conduit means to the separation means, thereby bypassing the reservoir.

23. A system according to claim 22 wherein the conduit means includes
- second conduit means between the separation means and the reservoir for conveying the separated constituent from the separation means to the reservoir for return to the door.

24. A system according to claim 22 wherein the conduit means includes
- a second reservoir,
- third conduit means between the separation means and the second reservoir for conveying the separated constituent into the second reservoir for return to the donor, and
- fourth conduit means between the second reservoir and the needle for returning the separated constituent from the second reservoir through the needle to the donor.

25. A system according to claim 24 wherein the first mentioned reservoir and the second reservoir comprise first and second compartments formed within a common housing.

26. A system for separating whole blood into its constituents comprising
- a single venepuncture needle,
- separation means for separating at least one constituent from the whole blood,
- a reservoir, and
- flow control means including
  - conduit means interconnecting the needle, the separation means, and the reservoir,
  - first pumping means located between the needle and the reservoir and being operable in a first mode for conveying blood away from the needle and in a second mode for conveying blood toward the needle, and
  - second pumping means for conveying blood into the separation means,
  - the flow control means being operative to place the first pumping means in its first mode for withdrawing whole blood from the donor through the needle and for collecting a quantity of the withdrawn whole blood in the reservoir while operation the second pumping means to convey another quantity of the withdrawn whole blood into the separation means,
  - the flow control means being further operative to place the first pumping means in its second mode for returning a separated constituent of the whole blood from the separation means to the donor through the needle in a path that isolates the returned constituent from the contents of the reservoir while operating the second pumping means to convey blood collected in the reservoir into the separation means, and
  - means for sequentially alternating operation of the first pumping means between its first and second modes to withdraw whole blood and return a separated constituent while operating the second pumping means to continuously supply blood into the separation means.

27. A system according to claim 26 wherein the conduit means includes means for collecting the separated constituent for return to the donor.

28. A system according to claim 27 wherein the separated constituent collection means comprises a second reservoir.

29. A system according to claim 27
wherein the flow control means includes third pumping means located between the separation means and the second reservoir for conveying blood from the separation means toward the second reservoir, and
wherein the first pumping means communicates with the second reservoir and is operative, when operated in its second mode, for conveying blood from the second reservoir toward the needle.

30. A system according to claim 27
wherein the reservoir includes a first and second compartment,
wherein the withdrawn whole blood is collected in the first compartment, and
wherein the separated constituent collection means comprises the second compartment.

31. A system according to claim 3
wherein the flow control means includes third pumping means located between the separation means and the second compartment for conveying blood from the separation means toward the second compartment, and
wherein the first pumping means communicates with the second compartment and is operative, when operative in its second mode, for conveying blood from the second compartment toward the needle.

32. A system according to claim 26
wherein, when the first pumping means is operated in its second mode, the second pumping means conveys whole blood from the reservoir to the separation means substantially free of mixing with the returned constituent.

33. A system according to claim 26
wherein, when the first pumping means is operated in its first mode, the second pumping means conveys the quantity of whole blood to the separation means by conveying whole blood from the reservoir to the separation means.

34. A system according to claim 26 wherein the conduit means comprises
- first conduit means between the needle and the reservoir for conveying a quantity of withdrawn whole blood to the reservoir in response to the operation of the first pumping means in its first mode,
- second conduit means between the reservoir and the separation means for conveying to the separation means a quantity of the whole blood collected in the reservoir in response to the operation of the second pumping means.

35. A system according to claim 34 wherein the conduit means includes
- a second reservoir,
- third conduit means between the separation means and the second reservoir for conveying the separated constituent to the second reservoir prior to return to the donor,
- fourth conduit means between the second reservoir and the needle for returning the separated constituent from the second reservoir through the needle to the donor in response to the operation of the first pumping means in its second mode.

36. A system according to claim 33 wherein the first mentioned reservoir and the second reservoir comprise first and second compartments formed within a common housing.

37. A system according to claim 35 wherein the flow control means includes third pumping means in the third conduit means.

38. A method for separating whole blood into its constituent comprising the steps of withdrawing whole blood from the donor through a single venepuncture needle and collecting a quantity of the withdrawn whole blood in a reservoir while at the same time conveying another quantity of the withdrawn whole blood constituent separator in a path that bypasses the reservoir, returning a separator constituent of the whole blood from the separator to the done through the same venepuncture needle while at the same time conveying blood from the reservoir to the separator, and alternating operation to withdraw whole blood and then return a separated constituent while continuously supplying blood to the separator.

39. A method for separating whole blood into its constituents comprising the steps of operating a first pump in a first direction to withdraw whole blood from the donor through a single venepuncture needle and collect a quantity of the withdrawn whole blood in a reservoir while at the same time operating a second pump to convey another quantity of the withdrawn whole blood constituent separator, operating the first pump in a second, opposite direction to return a separator constituent of the whole blood from the separator to the donor through the same venepuncture needle in a path that isolates the returned constituent from the contents of the reservoir while at the same time operating the second pump to convey blood collected in the reservoir to the separator, and alternating operation of the first pump in its first and second directions while operating the second pump to withdraw whole blood and return a separated constituent to the donor while continuously supplying blood to the separator.

40. A system for separating a cellular suspension into its constituents comprising a source of cellular suspension, an access conduit communicating with the cellular suspension, separation means for separating at least one constituent from the cellular suspension, a reservoir, conduit means interconnecting the source, the access conduit, and the separation means and being operative in a first mode for withdrawing the cellular suspension from the source through the access conduit and for collecting a quantity of withdrawn suspension in the reservoir while at the same time conveying another quantity of the withdrawn suspension to the separation means in a path that bypasses the reservoir, the conduit means being further operative in a second mode for returning a separated constituent of the suspension from the separation means to the source through the access conduit while at the same time conveying suspension from the reservoir to the separation means, and means for alternating operation of the conduit means between the first and second modes to withdraw the cellular suspension form the source and then return a separated constituent to the source while continuously supplying suspension to the separation means.

41. A system for separating a cellular suspension into its constituents comprising a source of the cellular suspension, an access conduit communicating with the source, separation means for separating at least one constituent from the cellular suspension, a reservoir, and flow control means including conduit means interconnecting the access conduit, the reservoir, and the separation means first pumping means located between the access conduit and the reservoir and being operable in a first mode to convey the cellular suspension away from the access conduit and in a second mode to convey the cellular suspension toward the access conduit, and second pumping means for conveying the cellular suspension into the separation means, the flow control means being operative to place the first pumping means in its first mode for withdrawing the cellular suspension from the source through the access conduit and for collecting a quantity of the withdrawn suspension in the reservoir while at the same time operating the second pumping means to convey another quantity of the withdrawn suspension to the separation means, the flow control means being further operative to place the first pumping means in its second mode for returning a separated constituent of the suspension from the separation means to the source through the access conduit in a path that isolated the returned constituent from the contents of the reservoir while at the same time operating the second pumping means to convey suspension collected in the reservoir to the separation means, and means for sequentially alternating operation of the first pumping means between its first and second modes to withdraw suspension from the source and then return a separated constituent to the source while operating the second pumping means to continuously supply suspension to the separating means.

42. A system for separating whole blood into its constituents comprising a single venepuncture needle, separation means for separating at least one constituent from whole blood, first and second reservoirs, each having a predetermined interior volume, first conduit means interconnecting the needle and the first reservoir, second conduit means interconnecting the first reservoir and the separation means, third conduit means interconnecting the separation means and the second reservoir, fourth conduit means interconnecting the second reservoir and the needle, first pumping means communicating with the first conduit means and the fourth conduit means, the first pumping means being operable in a first mode for conveying whole blood from the needle to the first reservoir and in a second mode of operation for conveying the separated constituent from the second reservoir to the needle for return to the donor, second pumping means communicating with the second conduit means for conveying whole blood from the reservoir to the separation means, and the interior volume of the first reservoir being sufficient, relative to the interior volume of the second reservoir, for sustaining a supply of whole blood continuously to the separation means during the operation of the second pumping means, without replenishment by the first conduit means and free of mixing with the separated constituent, while the separated constituent collected in the second reservoir is returned to the donor through the needle during the operation of the first pumping means in its second mode.

43. A system according to claim 42 wherein the first and second reservoirs comprise first and second compartments formed within a common housing.

44. Hemapheresis apparatus for separating whole blood collected from a donor into first and second blood constituents, comprising:

a separation device for separating whole blood into the first and second blood constituents;

a reservoir having discrete first and second compartments;

a single venepuncture needle for drawing whole blood from a donor;

a first conduit connecting between the needle and the reservoir for supplying whole blood from the needle to the first compartment of the reservoir during a blood collection cycle;

a second conduit connecting between the first compartment and the separation device for supplying whole blood from the first compartment to the separation device;

an outlet from the separation device for the separated first blood constituent;

a third conduit connecting between the separation device and the reservoir for supplying the second blood constituent to the second compartment;

a fourth conduit connecting between the reservoir and the venepuncture needle for returning the second blood constituent from the second compartment through the needle to the donor for reinfusion during a blood reinfusion cycle first pumping means for conveying blood through the first conduit into the first compartment; and second pumping means for conveying blood from the first compartment to the separation device;

whereby blood may be alternately collected from a donor in the first compartment of the reservoir and reinfused into the donor from the second compartment of the reservoir while blood is simultaneously and continuously supplied from the first compartment of the reservoir to the separation device.

45. Hemapheresis apparatus according to claim 44 and further including third pumping means for conveying the second blood constituent through the third conduit into the second compartment.

46. Hemapheresis apparatus according to claim 44 wherein the first pumping means is reversible for conveying the second blood constituent from the second compartment to the need for reinfusion into the donor.

47. A harness set for a hemapheresis instrument comprising:

a separation device for processing blood fluid;

a housing defining a reservoir including discrete side-by-side first and second compartments separated by a partition wall, the partition wall having at least two laterally offset portions projecting into the compartments in vertical misalignment with each other, the reservoir further including first and second outlet ports generally located at the lower ends of the first and second compartments, respectively, as well as first and second inlet ports generally located at the upper ends of the first and second compartments, respectively;

a venepuncture needle;

first means for establishing blood fluid communication between said needle and the first inlet port located in said first compartment of said reservoir;

second means for establishing blood fluid communication between the first outlet port located in said first compartment of said reservoir and said separator;

third means for establishing blood fluid communication between said separator and the second inlet port located in said second compartment of said reservoir; and further means for establishing blood fluid communication between the second outlet port located in said second compartment and said venepuncture needle, whereby blood fluid may be collected from a donor in the first reservoir compartment and returned to the needle from the second reservoir compartments while blood fluid is simultaneously and continuously supplied from said first reservoir compartment to said separation device.

48. A harness set according to claim 47 wherein the misaligned portions of the partition wall are laterally staggered relative to each other and located so that portions of the first compartment lie in vertical registration with portions of the second compartment.

49. Hemapheresis apparatus for separating whole blood collected from a donor into first and second blood constituents, comprising:

a separation device for separating whole blood into the first and second blood constituents;

a reservoir including discrete side-by-side first and second compartments separated by a partition wall, the partition wall having at least two laterally offset portions projecting into the compartments in vertical misalignment with each other, the reservoir further including first and second outlet ports generally located at the lower ends of the first and second compartments, respectively, as well as first and second inlet ports generally located at the upper ends of the first and second compartments, respectively;

a single venepuncture needle for drawing whole blood from a donor;

a first conduit connecting between said needle and the first inlet port located in the first compartment of said reservoir for supplying whole blood from said needle to the first compartment during a blood collection cycle;

a second conduit connecting between the first outlet port of said first compartment and said separation device for supplying whole blood from said first compartment to said separation device;

an outlet from said separation device for the separated first blood constituent;

a third conduit connecting between said separation device and the second inlet port located in the second compartment of said reservoir for supplying the second blood constituent to said second compartment; and a fourth conduit connecting between the second outlet port located in the second compartment of said reservoir and said venepuncture needle for returning the second blood constituent from said second compartment through said needle to the donor for reinfusion during a blood reinfusion cycle whereby blood may be alternately collected from a donor in the first compartment of said reservoir and reinfused into the donor from the second compartment of said reservoir while blood is simultaneously and continuously supplied from the first compartment of said reservoir to said separation device.

50. Hemapheresis apparatus according to claim 49 wherein the misaligned portions of the partition wall are laterally staggered relative to each other and located so that portions of the first compartment lie in vertical registration with portions of the second compartment.

51. Hemapheresis apparatus according to claim 50 and further including means for sensing the blood level in each of the first and second compartments adjacent their upper and ports, the sensing means lying in vertical alignment is registry with the vertically registering portions of the first and second compartments.

52. Hemapheresis apparatus for separating whole blood collected from a donor into first and second blood constituents, comprising:

a separation device for separating whole blood into the first and second blood constituents;

a reservoir having discrete first and second compartments, the reservoir having first and second outlet ports generally located at the lower ends of the first and second compartments, respectively, as well as first and second inlet ports generally located at the upper ends of the first and second compartments, respectively;

a single venepuncture needle for drawing whole blood from a donor;

a first conduit connecting between said needle and the first inlet port located in the first compartment of said reservoir for supplying whole blood from said needle to the first compartment during a blood collection cycle;

a second conduit connecting between the first outlet port of said first compartment and said separation device for supplying whole blood from said first compartment to said separation device;

an outlet from said separation device for the separated first blood constituent;

a third conduit connecting between said separation device and the second inlet port located in the second compartment of said reservoir for supplying the second blood constituent to said second compartment;

a fourth conduit connecting between the second outlet port located in the second compartment of said reservoir and said venepuncture needle for returning the second blood constituent from said second compartment through said needle to the donor for reinfusion during a blood reinfusion cycle; and pumping means for alternatively collecting blood from a donor in the first compartment of said reservoir and reinfusing blood into the donor from the second compartment of said reservoir while blood is simultaneously and continuously supplied from the first compartment of said reservoir to said separation device, the pumping means including first means for pumping blood through the first conduit into the first compartment, second means for pumping blood from the first compartment to the separation device, and third means for pumping the second blood constituent through the third conduit into the second compartment.

53. Hemapheresis apparatus according to claim 52 wherein the first means is reversible for pumping the second blood constituent from the second compartment to the needle for reinfusion into the donor.

54. Hemapheresis apparatus according to claim 52 and further including means for sensing the fluid level in each of the first and second compartments, the sensing means lying in vertical registration with each other.

55. Hemapheresis apparatus according to claim 54 wherein the pumping means operates the first, second, and third means so that the pumping rate of the first means is substantially equal to the pumping rate of the second and third means.

56. Hemapheresis apparatus for separating whole blood collected from a donor into first and second blood constituents, comprising:

a separation device for separating whole blood into the first and second blood constituents, a reservoir discrete first and second compartments separated by a partition wall and including means on the wall defining a port for establishing communication between the two compartments, the reservoir having first and second outlet ports generally located at the lower ends of the first and second compartments, respectively, as well as first and second inlet ports generally located at the upper ends of the first and second compartments, respectively;

a single venepuncture needle for drawing whole blood from a donor;

a first conduit connecting between said needle and the first inlet port located in the first compartment of said reservoir for supplying whole blood from said needle to the first compartment during a blood collection cycle;

a second conduit connecting between the first outlet port of said first compartment and said separation device for supplying whole blood from said first compartment to said separation device;

an outlet from said separation device for the separated first blood constituent;

a third conduit connecting between said separation device and the second inlet port located in the second compartment of said reservoir for supplying the second blood constituent to said second compartment; and a fourth conduit connecting between the second outlet port located in the second compartment of said reservoir and said venepuncture needle for returning the second blood constituent from said second compartment through said needle to the donor for reinfusion during a blood reinfusion cycle whereby blood may be alternatively collected from a donor in the first compartment of said reservoir and reinfused into the donor from the second compartment of said reservoir while blood is simultaneously and continuously supplied from the first compartment of said reservoir to said separation device.

57. Hemapheresis apparatus according to claim 56 wherein the compartments lie side-by-side and the port is located in a lower portion of the partition wall.

58. Apparatus according to claim 21 or 23 or 26 or 32 wherein said first and fourth conduits are connected one to the other.

* * * * *

UNITED STATES PATENT AND TRADEMARK OFFICE
CERTIFICATE OF CORRECTION

PATENT NO. : 5,188,588
DATED : February 23, 1993
INVENTOR(S) : Schoendorfer et al It is certified that error appears in the above-indentified patent and that said Letters Patent is hereby corrected as shown below:

| | |
|---|---|
| Column 13, Line 46 | Before "second" delete "a" |
| Column 13, Line 51 | Change "end" to -- ends -- |
| Column 15, Line 35 | Delete "while" and substitute -- whole -- |
| Column 16, Line 7 | Delete "infusing" and substitute -- reinfusing -- |
| Column 16, Line 26 | After "said" delete "from" |
| Column 16, Line 38 | After "withdrawn" insert -- whole -- |
| Column 16, Line 43 | Delete "separating" and substitute -- separated -- |
| Column 16, Line 46 | After "means," insert -- and -- |
| Column 17, Line 16 | Delete "door" and substitute -- donor -- |
| Column 17, Line 36 | After "from" delete "the" |
| Column 17, Line 53 | Delete "operation" and substitute -- operating -- |
| Column 18, Line 27 | After "claim" delete "3" and substitute -- 30 -- |
| Column 18, Line 35 | Delete "operative" and substitute -- operated -- |
| Column 19, Line 4 | After "claim" delete "33" and substitute -- 35 -- |
| Column 19, Line 12 | Change "constituent" to -- constituents -- |
| Column 19, Line 17 | After "blood" insert -- to a blood -- |
| Column 19, Line 19 | Delete "separator" and substitute -- separated -- |
| Column 19, Line 20 | Delete "done" and substitute -- donor -- |
| Column 19, Line 34 | After "blood" insert -- to a blood -- |
| Column 19, Line 37 | Delete "separator" and substitute -- separated -- |
| Column 19, Line 61 | Before "withdrawn" insert -- the |
| Column 20, Line 6 | Delete "form" and substitute -- from -- |
| Column 20, Line 41 | Delete "isolated" and substitute -- isolates -- |
| Column 20, Line 53 | Delete "separating" and substitute -- separation -- |
| Column 21, Line 58 | Delete "alternately" and substitute -- alternatively -- |

UNITED STATES PATENT AND TRADEMARK OFFICE
CERTIFICATE OF CORRECTION

PATENT NO. : 5,188,588

DATED : February 23, 1993

INVENTOR(S) : Schoendorfer et al.

It is certified that error appears in the above-identified patent and that said Letters Patent is hereby corrected as shown below:

```
Column 22, Line 38    Change "compartments" to -- compartment --
Column 23, Line 20    Delete "alternately" and substitute --
                      alternatively --
Column 23, Line 35    Delete "ports" and substitute -- portions --
Column 24, Line 23    Delete "needle" and substitute -- need --
Column 24, Line 39    After "reservoir" insert -- having --
Column 26, Line  7    Change the claim dependency to read -- 47 or 49
                      or 52 or 56 --
```

Signed and Sealed this

Twenty-sixth Day of April, 1994

Attest:

BRUCE LEHMAN

Attesting Officer    Commissioner of Patents and Trademarks